(12) United States Patent
Svensson

(10) Patent No.: US 9,786,093 B2
(45) Date of Patent: Oct. 10, 2017

(54) RADIOTHERAPY METHOD, COMPUTER PROGRAM AND COMPUTER SYSTEM

(71) Applicant: RaySearch Laboratories AB, Stockholm (SE)

(72) Inventor: Stina Svensson, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 15/381,382

(22) Filed: Dec. 16, 2016

(65) Prior Publication Data

US 2017/0178391 A1    Jun. 22, 2017

(30) Foreign Application Priority Data

Dec. 18, 2015   (EP) .................................. 15201272

(51) Int. Cl.
| | |
|---|---|
| G06F 17/50 | (2006.01) |
| G06T 15/00 | (2011.01) |
| G06T 15/20 | (2011.01) |
| A61N 5/10 | (2006.01) |
| G06F 19/00 | (2011.01) |
| G06T 11/00 | (2006.01) |
| G06T 19/20 | (2011.01) |
| G06T 3/00 | (2006.01) |
| G06T 7/33 | (2017.01) |

(52) U.S. Cl.
CPC ............ *G06T 15/20* (2013.01); *A61N 5/1039* (2013.01); *G06F 19/3437* (2013.01); *G06T 3/0068* (2013.01); *G06T 7/344* (2017.01); *G06T 11/003* (2013.01); *G06T 19/20* (2013.01); *G06T 2207/10081* (2013.01); *G06T 2207/10088* (2013.01); *G06T 2207/30196* (2013.01)

(58) Field of Classification Search
None
See application file for complete search history.

(56) References Cited

U.S. PATENT DOCUMENTS

| | | | |
|---|---|---|---|
| 5,633,951 A | 5/1997 | Moshfeghi | |
| 6,266,453 B1 * | 7/2001 | Hibbard | ............... G06T 3/0006 382/131 |

(Continued)

FOREIGN PATENT DOCUMENTS

WO    WO-03/105069 A1    12/2003

OTHER PUBLICATIONS

Zhen, Xin, et al. "Deformable image registration of CT and truncated cone-beam CT for adaptive radiation therapy." Physics in medicine and biology 58.22 (2013): 7979.*

Zamyatin, Alexander A., and Satoru Nakanishi. "Extension of the reconstruction field of view and truncation correction using sinogram decomposition." Medical physics 34.5 (2007): 1593-1604.*

(Continued)

*Primary Examiner* — Sultana M Zalalee
(74) *Attorney, Agent, or Firm* — Drinker Biddle & Reath LLP

(57) ABSTRACT

A method of obtaining a 3D image of a part of a patient's body is disclosed, based on a fraction image having a limited field-of-view and complementing this with information from a planning image having a greater field-of-view. In the area outside of the fraction image field-of-view, contour and anatomical data from the planning image are used to complement the fraction image, by means of a contour-guided deformable registration between the planning image and the fraction image.

11 Claims, 3 Drawing Sheets

(56) References Cited

U.S. PATENT DOCUMENTS

| | | | | |
|---|---|---|---|---|
| 2006/0262112 | A1* | 11/2006 | Shimada | G06T 17/00 345/419 |
| 2007/0053491 | A1* | 3/2007 | Schildkraut | A61N 5/1049 378/65 |
| 2007/0189591 | A1* | 8/2007 | Lu | A61N 5/103 382/128 |
| 2007/0195923 | A1* | 8/2007 | Netsch | G06T 11/005 378/4 |
| 2010/0195890 | A1 | 8/2010 | Berlinger et al. | |
| 2011/0178389 | A1* | 7/2011 | Kumar | A61B 5/055 600/411 |
| 2012/0035888 | A1* | 2/2012 | Shin | G06F 19/3437 703/1 |
| 2012/0294497 | A1 | 11/2012 | Zankowski | |

OTHER PUBLICATIONS

Lee, Jiseoc, and Seungryong Cho. "Improving image accuracy of region of interest in cone-beam CT using prior image." World Congress on Medical Physics and Biomedical Engineering May 26-31, 2012, Beijing, China. Springer Berlin Heidelberg, 2013.*

Wang, Jing, and Xuejun Gu. "High-quality four-dimensional cone-beam CT by deforming prior images." Physics in medicine and biology 58.2 (2012): 231.*

European Search Report dated Jun. 3, 2016 for European Application No. 15201272.0.

Ruchala Kenneth J. et al., "Methods for Improving Limited Field-of-View Radiotherapy Reconstructions Using Imperfect a priori Images," Medical Physics, AIP, Melville, NY, US, vol. 29, No. 11, pp. 2590-2605, Nov. 1, 2002.

* cited by examiner

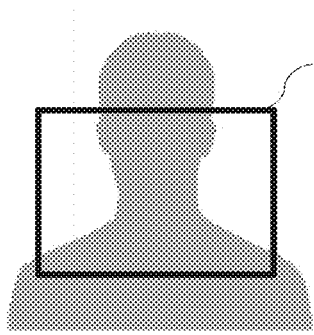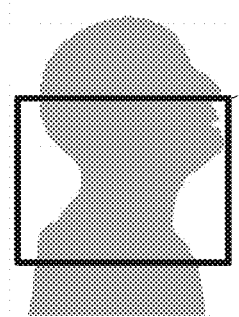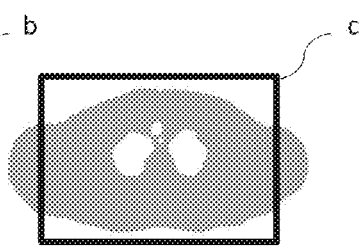
Fig. 1a  Fig. 1b  Fig. 1c
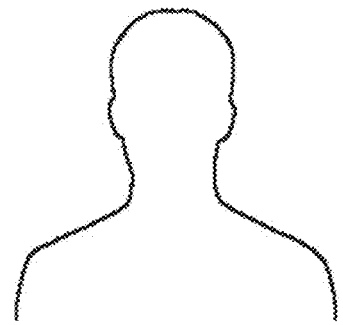
Fig. 1d
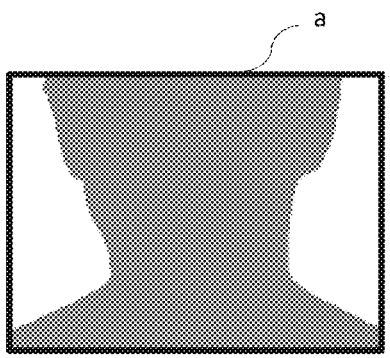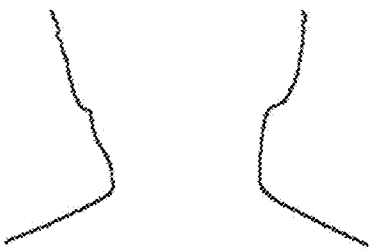
Fig. 2a  Fig. 2b

RADIOTHERAPY METHOD, COMPUTER PROGRAM AND COMPUTER SYSTEM

RELATED APPLICATION DATA

This application claims priority under 35 U.S.C. §119 and/or §365 to European Patent Application No. 15201272.0 filed Dec. 18, 2015, the entire contents of which is incorporated herein by reference.

TECHNICAL FIELD

The present invention relates to image guided radiotherapy.

BACKGROUND AND RELATED ART

Radiotherapy treatment is generally distributed to a patient in a number of sessions, or fractions. Before the treatment starts, a planning image of the patient is obtained. The planning image provides input data to a treatment plan, which defines the treatment to be given to the patient. Before each session a fraction image is obtained, to assist in positioning the patient with respect to the treatment unit before the delivery. The fraction images can also be used to assess the dose actually delivered to the patient during the session and also to study changes in patient-geometry that have occurred since the planning image was acquired. Such changes are important for treatment evaluation and the result of the evaluation may lead to a decision that modifications of the treatment plan are required. In the context of this description, both the planning image and the fraction images are 3D images constructed from a number of 2D images constituting projections of the patient's body.

Dose planning requires information about the location of the various organs and also about their material properties, such as density and/or atomic composition. Density information is used for dose planning. If photon radiotherapy is used, the density and atomic composition determine the attenuation of the radiation. If ion radiotherapy such as proton radiotherapy is used, the density and atomic composition determine the stopping power, which affects the distance that the ions will travel within the patient's body. For the initial planning, this information is taken from the planning image. The fraction images are typically used to determine the new boundaries of the regions of interest in order to aim the radiation beams correctly.

Therefore, the planning image should comprise information not only about the contours but also about the material properties of each region of interest. As the geometry of the tumor and other tissues changes during the course of therapy, the fraction images are used to obtain up-to-date contour information. However, the fraction images may have considerably less information than the planning images. For example, a fan beam CT scan (referred to in this document as CT) may be used for the planning image while Cone Beam CT (CBCT) scans are used for the fraction images. CT images comprise all the information needed for dose planning but are relatively expensive and involve a higher radiation dose to the patient than CBCT. CBCT on the other hand, with the advantage of giving lower radiation dose to the patient and also being a less expensive imaging system, does not always provide reliable information about material properties and in particular is subject to distortion such as cupping distortion, where the intensity of the image is misrepresented near the edges of the image. Other imaging technologies involve even less or no radiation but do not provide all the information necessary for proper treatment planning.

Typically, the field-of-view for a CBCT image does not cover the full patient outline. This means that when computing dose based on a fraction image the densities for the parts outside of the field-of-view need to be estimated for dose computation. One solution would be to superimpose the patient's outline from the planning image onto the fraction image and assuming that it has the same properties as water. Water is a reasonable compromise, as it is a good approximation for most parts of the body, but this solution still causes inaccuracies in the dose computation.

Ruchala, Olivera, Kapatoes, Reckwerdt and Mackie: Methods for improving limited field-of-view radiotherapy reconstruction using imperfect a priori images, Medical Physics 29, 2590 (2002); doi: 10.1118/1.1513163, discloses a method of handling this problem working directly in the 2D images which are afterwards used to construct the 3D image. The method proposed in this document is not applicable when working directly with 3D images. Typically, the treatment planning system does not provide access to the 2D images so any changes made through these systems must be made in the 3D image.

SUMMARY OF THE INVENTION

It is therefore an object of the invention to improve the accuracy of dose computation working in 3D images, when the fraction images do not cover the whole outline of the patient.

This object is achieved according to the invention by a method of obtaining a 3D composite image of at least a first part of a patient's body, comprising the steps of

- obtaining a 3D planning image corresponding to the first portion of the patient's body and having a first field-of-view,
- obtaining a 3D fraction image of the first portion of the patient's body, the fraction image having a second field-of-view which is limited in at least one dimension compared to the first field-of-view, creating a model outline including at least one area of the patient's body included in the first field-of-view but not in the second field-of-view,
- appending the model outline to the fraction image, to include at least one outlined portion in the fraction image outside the second field-of-view to obtain an intermediate image,
- performing a deformable registration between the outline of the planning image and the outline of the fraction image,
- using the result of the deformable registration to include material information from the area in the planning image inside of the outlined portion outside the second field-of-view in the intermediate image, to obtain a composite image.

In this way, a composite image is obtained, comprising up-to-date information from the fraction image in the areas where such information is available, and anatomical information based on the planning image but adapted to the fraction image, in areas outside the second field-of-view.

Using the method and computer program according to the invention, the information from the planning image, concerning the parts of the patient's body that are outside of the field-of-view of the fraction image, are adapted to the actual geometry of the fraction image and added to the fraction image. This is achieved by elastic registration of the fraction image with the planning image. Elastic registration is also referred to as deformable registration.

In a preferred embodiment, a statistical shape model outline based on the planning image is used as the model outline, and the method comprises the step of adapting the model outline to the fraction image. A cost function based on a distance transform may be used for adapting the model outline to the fraction image.

Before adapting the model outline to the fraction image, an initial overlap between the model outline and the fraction image is preferably determined. This may be achieved by using an automatic rigid registration algorithm between the planning image and the fraction image. The images may also be superimposed based on a visual assessment of the initial overlap, or in any other suitable way.

Preferably, the outlined portion is selected in such a way that the field-of-view of the composite image corresponds to the first field-of-view, to use the data from the planning image to the greatest possible extent.

The method will yield the best results if the planning image is an image of the patient, taken at an earlier point in time than the fraction image. The planning image may also be another suitable image, such as an atlas image.

The material information taken from the planning image typically includes density information, atomic composition and/or anatomical information, depending on what is useful for a particular application.

The invention also relates to a computer program product, preferably on a carrier, for controlling a computer, said computer program product comprising computer-readable code arranged to cause the computer to perform the method according to any one of the preceding claims.

The method is intended for use in connection with a radiotherapy apparatus. The invention also relates to a computer system comprising a processor, a data memory and a program memory. The data memory is arranged to hold at least one planning image and/or at least one fraction image and the program memory is arranged to hold a computer program product as defined above, in such a way that the computer program product can be used to control the processor. As will be understood, the inventive method itself can be performed in any computer having the necessary software installed.

The planning image and the fraction image should be anatomical images, such as CT or MRI images. Further, the planning image and the fraction image preferably comprise the same type of data. This means that if the planning image is a CT image, the fraction image should be a CT or CBCT image. If the planning image is an MRI image, the fraction image should be an MRI image. It is also possible to create a synthetic CT image from an MRI image, that is, an image comprising the same types of data as a CT image. Such a synthetic CT image could be used as a planning or fraction image, together with other CT or CBCT images as planning or fraction images.

BRIEF DESCRIPTION OF THE DRAWINGS

In the following, the invention will be described in more detail, with reference to the appended drawings, in which:

FIGS. 1a, 1b and 1c show three different views of a planning image of a patient.

FIG. 1d shows a model outline of the planning image.

FIGS. 2a and b show a fraction image of a patient and a fraction outline of the fraction image, respectively.

DETAILED DESCRIPTION OF PREFERRED EMBODIMENTS

FIGS. 1a, 1b and 1c show a coronal, a sagittal, and a transversal slice, respectively, of a 3D planning image having a first field-of-view. The planning image comprises anatomical information about the patient. In each of the images 1a-1c, the field-of-view of the corresponding projection of a fraction image is indicated as a solid rectangle, a, b and c, respectively. FIG. 1d shows a transversal slice of the patient outline on the planning image, which is used as a model outline.

FIG. 2a shows a coronal slice of a 3D fraction image, comprising the same type of data as the planning image but having a second field-of-view that is limited compared to the first field-of-view, as indicated by the rectangle in FIG. 1a. In particular, the top of the patient's head and an area from the shoulders down are not included. Typically, the fraction image is of the same patient as the planning image, but taken at a later point in time. FIG. 2b shows the patient outline from the fraction image. This outline is obtained with known methods and will be referred to in this document as the fraction outline.

The aim is to obtain an image having all the data from the fraction image but a greater field-of-view than the second field-of-view. In the area outside of the second field-of-view, contour and anatomical data from the planning image are used to complement the fraction image. Such a fraction image, complemented with an approximate outline of parts of the patient's body that are outside of the field-of-view of the fraction image is referred to in this document as an enhanced fraction image. An enhanced fraction image, in which material information has been added outside of the field-of-view of the fraction image based on information from the planning image, is referred to as a composite image.

Figure 3:
FIG. 3 illustrates a cost map function from the fraction outline for adaptation to the model outline.

FIG. 3 illustrates a cost map based on a distance transform of the fraction outline to adapt the model outline to the fraction outline. The solid contour corresponds to the fraction outline. The dashed contours on both sides of the solid contour indicate a first distance from the fraction outline, corresponding to a first cost level. The dotted contours on both sides of the dashed contours indicate a second distance from the fraction outline, corresponding to a second cost level. The cost level increases with increased distance from the fraction outline.

Figure 4:
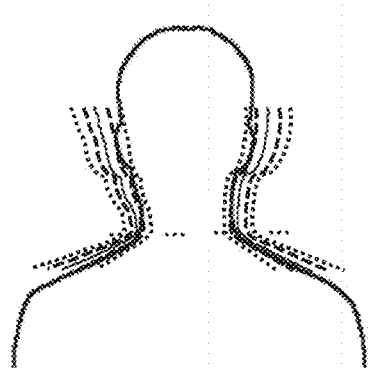
FIG. 4 shows an initial position of the model outline relative to the cost map function.

FIG. 4 illustrates an initial superpositioning of the model outline of FIG. 1d on the cost map of FIG. 3. This may be based, for example, on a rigid registration between the planning image and the fraction image, known per se, on visual approximation or on another suitable method.

Figure 5:
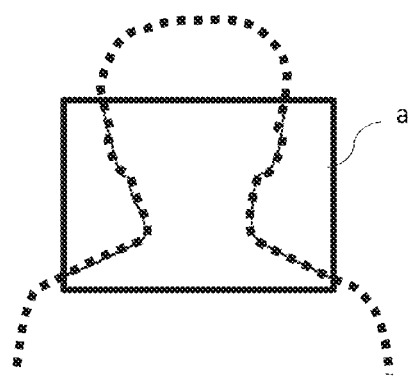
FIG. 5 shows the model outline adapted to the fraction outline.

FIG. 5 illustrates, as a dashed line, an altered model outline, which has been adapted to the fraction outline for the parts inside the second field-of-view, which has also caused changes outside the second field-of view. This is the outline of the enhanced fraction image, adapted based on the cost map shown in FIG. 3. The second field-of-view is indicated by the solid rectangle, which is again denoted a.

Figure 6:
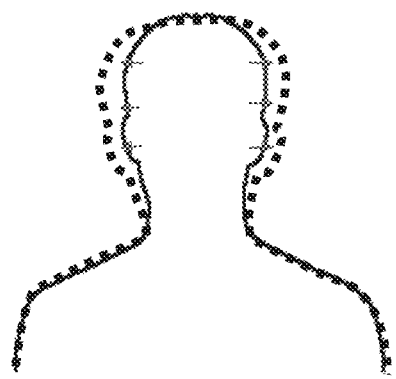
FIG. 6 illustrates a contour-guided deformable registration between the model outline and the enhanced fraction image outline.

FIG. 6 illustrates a contour-guided deformable registration between the model outline of FIG. 1d, shown as a solid line and the enhanced fraction outline of FIG. 5, shown as a dashed line. How to perform a contour-guided deformable registration is known to the skilled person.

Figure 7A:
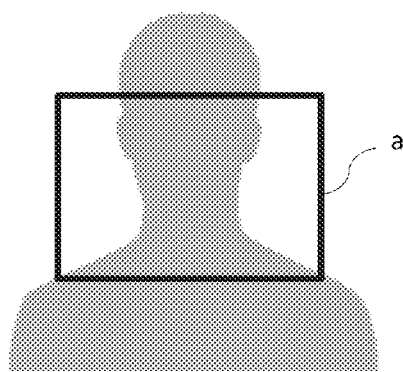
FIGS. 7a-c illustrate the enhanced fraction image with values inside field-of-view from the fraction image and values outside field-of-view deformably mapped from the planning image.
Figure 7B:
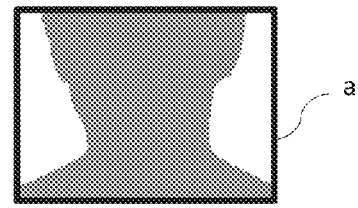
Figure 7C:
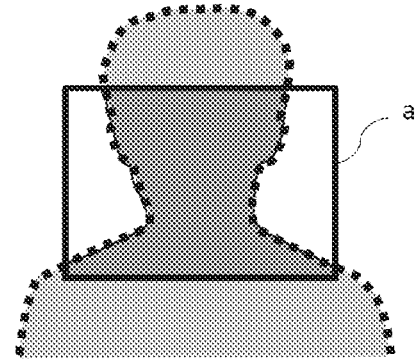

FIG. 7 illustrates the planning image, fraction image and composite image, i.e., the enhanced fraction image, discussed above. On the left, denoted 7a), the planning image of FIG. 1a is shown, with the field-of-view of the fraction image superimposed, as a solid rectangle denoted a. On the right, denoted 7b), the fraction image of FIG. 2a is shown. In the centre, denoted 7c), a composite image is shown. Inside the field-of-view of the fraction image, illustrated by the solid rectangle a, the composite image has the same anatomical data as the fraction image. Outside the field-of-view of the fraction image, the composite image includes anatomical data which is deformably mapped from the planning image.

Figure 8:
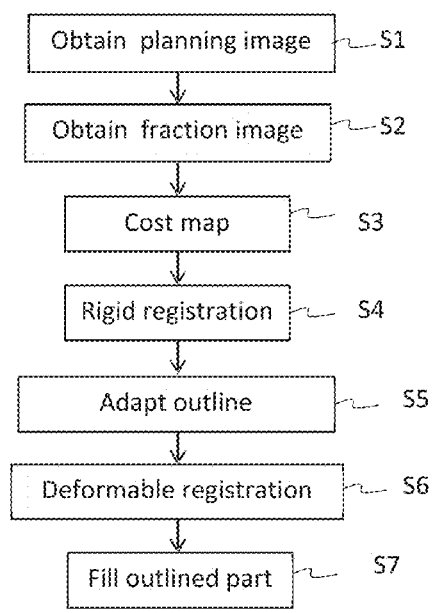
FIG. 8 is a flow chart of the method according to the invention.

FIG. 8 is a flow chart of an embodiment of the inventive method, to be performed before a treatment session. Prior to this, a 3D planning image, typically a CT image, has been obtained and a treatment plan has been developed.

In a first step S1, a 3D planning image is obtained. Typically the planning image is an anatomical 3D image of the patient. It would also be possible to use an atlas image as a planning image. A statistical shape model outline is created based on the planning image.

In a second step S2, a 3D fraction image is obtained, to prepare for a treatment session. The fraction image should have the same type of data as the planning image, and typically has a more limited field-of-view than the planning image. A representation of the patient outline in the fraction image is obtained.

In a third step S3, a cost map is obtained from the fraction outline.

In a fourth step S4, a rigid registration is performed between the planning image and the fraction image. This gives a first approximation of the patient's outline in the parts not included in the fraction image, and of the best way to superimpose the model outline to the fraction image. In this way a starting point for patient outline in the enhanced fraction image is created. The order of steps S3 and S4 is not important.

In a fifth step S5, the model outline is adapted to the edges of the fraction outline, i.e., the contour that is strictly within the field-of-view of the fraction image obtained in step S2. This is typically done using the cost map determined in step S3. The starting point is the superposition determined in step S4. Each individual point in the model outline can move towards a lower cost, under the constraint that model shape is preserved. The result of this is the patient outline for the enhanced fraction image shown in FIG. 5.

In a sixth step S6, a contour-guided deformable registration is performed using the fraction outline and the outline of the planning image.

In a seventh step S7, the result of the deformable registration is used to fill the outlined parts of the enhanced fraction image having no data or standard data, i.e., the parts outside the second field-of-view. The result of this is the composite image denoted c) in FIG. 7, where information inside the enhanced fraction outline but outside the field-of-view is based on data from the planning image, using the deformable registration.

Figure 9:
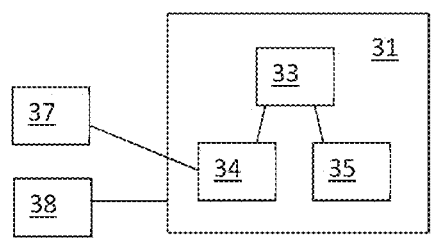
FIG. 9 illustrates schematically a computer system that may be used according to the invention.

FIG. 9 is a schematic representation of a computer system in which the inventive method may be performed. A computer 31 comprises a processor 33, a data memory 34 and a program memory 35. The data memory 34 is arranged to hold at least a first image to be used as a planning image second image to be used as a fraction image. The images may be received from CT or MRI imaging systems 37 or from some other unit by any known communication method. Typically the images will be received from different imaging systems although only one is indicated in FIG. 9. Preferably, a user input means 38 is also present, in the form of a keyboard, a mouse, a joystick, voice recognition means or any other available user input means.

The data memory 34 may also hold other data, such as a treatment plan and other data related to the treatment. The treatment plan may be generated in the computer 31, or received from another storage means in any way known in the art.

As will be understood, the data memory 34 is only shown schematically. There may be several data memory units, each holding one or more different types of data, for example, one data memory for the treatment plan, one for the CT scans, etc.

The program memory 35 holds a computer program arranged to control the processor to perform the method as defined in FIG. 8. It will be understood that not all of the steps of the method of FIG. 8 are necessarily performed in the computer 31.

The invention claimed is:

1. A method of obtaining a 3D composite image of at least a first portion of a patient's body, comprising the steps of:
    obtaining a 3D planning image corresponding to the first portion of the patient's body and having a first field-of-view,
    obtaining a 3D fraction image of the first portion of the patient's body, the fraction image having a second field-of-view which is limited in at least one dimension compared to the first field-of-view,
    creating a model outline including at least one area of the patient's body included in the first field-of-view but not in the second field-of-view,
    appending the model outline to the fraction image, to include at least one outlined portion in the fraction image which is outside the second field-of-view to obtain an intermediate image,
    performing a deformable registration between the outline of the planning image and the outline of the fraction image,
    using the result of the deformable registration to include material information from the area in the planning image inside of the outlined portion in the intermediate image, to obtain a composite image.

2. A method according to claim 1, wherein a statistical shape model outline based on the planning image is used as the model outline, the method comprising the step of adapting the model outline to the fraction image.

3. A method according to claim 1, wherein a cost function based on a distance transform is used for adapting the model outline to the fraction image.

4. A method according to claim 1, comprising the step of performing a rigid registration between the planning image and the fraction image to determine an initial overlap between the model outline and the fraction image, before adapting the model outline to the fraction image.

5. A method according to claim 1, wherein the outlined portion is selected in such a way that the field-of-view of the composite image corresponds to the first field-of-view.

6. A method according to claim 1, wherein the planning image is an image of the patient, taken at an earlier point in time than the fraction image.

7. A method according to claim 1, wherein the 3D planning image is a CT image and the fraction image is a CT or CBCT image.

8. A method according to claim 1, wherein the planning image is an MRI image and the fraction image is an MRI image.

9. A method according to claim 1, wherein the material information includes density information, atomic composition and/or anatomical information.

10. A computer program product encoded in a non-transitory computer-readable medium for controlling a computer, said computer program product comprising computer-readable code arranged to cause the computer to perform the method according to claim 1.

11. A computer system comprising a processor, a data memory and a program memory, said data memory being arranged to hold at least one planning image and/or at least one fraction image and said program memory being arranged to hold a computer program product comprising computer-readable code that causes the computer to perform the method according to claim 1 when executed, in such a way that the computer program product can be used to control the processor.

* * * * *